(12) United States Patent
Turner et al.

(10) Patent No.: US 11,839,711 B2
(45) Date of Patent: Dec. 12, 2023

(54) PERFUSION SYSTEM WITH HEAT EXCHANGER

(71) Applicant: Spectrum Medical Ltd., Gloucester (GB)

(72) Inventors: Stephen Turner, Gloucester (GB); Benjamin David Garbutt, Gloucester (GB)

(73) Assignee: Spectrum Medical Ltd, Gloucester (GB)

( * ) Notice: Subject to any disclaimer, the term of this patent is extended or adjusted under 35 U.S.C. 154(b) by 0 days.

(21) Appl. No.: 17/743,655

(22) Filed: May 13, 2022

(65) Prior Publication Data

US 2022/0265911 A1    Aug. 25, 2022

Related U.S. Application Data

(63) Continuation of application No. 16/311,938, filed as application No. PCT/GB2017/051898 on Jun. 29, 2017, now abandoned.

(30) Foreign Application Priority Data

| Jun. 30, 2016 | (GB) | 1611409 |
| Apr. 25, 2017 | (GB) | 1706563 |
| May 17, 2017 | (GB) | 1707935 |

(51) Int. Cl.
*A61M 1/16* (2006.01)
*A61M 1/36* (2006.01)

(52) U.S. Cl.
CPC ........ *A61M 1/1698* (2013.01); *A61M 1/3664* (2013.01); *A61M 1/3666* (2013.01);
(Continued)

(58) Field of Classification Search
CPC .............. A61M 1/1698; A61M 1/3664; A61M 1/3666; A61M 1/369; A61M 2205/0205; A61M 2205/36
See application file for complete search history.

(56) References Cited

U.S. PATENT DOCUMENTS

| 3,064,649 A | 11/1962 | Fuson |
| 6,423,268 B1 * | 7/2002 | King ................... A61M 1/3664 210/260 |

(Continued)

FOREIGN PATENT DOCUMENTS

| EP | 0 228 968 | 7/1987 |
| EP | 0445079 A | 9/1991 |

(Continued)

OTHER PUBLICATIONS

European Patent Office, International Search Report and Written Opinion for PCT application No. PCT/GB2017/051898 dated Jul. 11, 2017 (16 pages).

(Continued)

*Primary Examiner* — Philip R Wiest
(74) *Attorney, Agent, or Firm* — Sunstein LLP

(57) ABSTRACT

A method of controlling thermal transfer in a perfusion system heat exchanger of an extracorporeal fluid treatment device for conditioning an extracorporeal patient fluid for administration to a patient comprises a step of providing a perfusion system heat exchanger, wherein the perfusion system heat exchanger comprises a first fluid passage for a liquid heat transfer medium and a second fluid passage for the extracorporeal patient fluid to be temperature-controlled via exchange of thermal energy with the heat transfer medium, and a step of providing the heat transfer medium through the first fluid passage. The heat transfer medium comprises a component with anti-microbial properties, such as glycol. The provision of antimicrobial fluid reduces the (Continued)

risk of microbe contamination of the extracorporeal fluid, and hence the risk of clinical complications.

16 Claims, 8 Drawing Sheets

(52) U.S. Cl.
CPC ..... *A61M 1/369* (2013.01); *A61M 2205/0205* (2013.01); *A61M 2205/36* (2013.01)

(56) References Cited

U.S. PATENT DOCUMENTS

| | | | |
|---|---|---|---|
| 8,475,509 B2 | 7/2013 | Dae | |
| 8,545,754 B2* | 10/2013 | Carpenter | A61M 1/1698 604/4.01 |
| 10,821,219 B2* | 11/2020 | Hu | A61M 1/3666 |
| 2006/0293734 A1* | 12/2006 | Scott | A61M 1/369 607/113 |
| 2007/0197951 A1 | 8/2007 | Mannlein et al. | |
| 2016/0243347 A1* | 8/2016 | Geiger | A61M 1/14 |
| 2017/0267907 A1* | 9/2017 | Knott | C09K 5/10 |

FOREIGN PATENT DOCUMENTS

| | | |
|---|---|---|
| JP | H04-95043 U | 8/1992 |
| JP | H04-218166 A | 8/1992 |
| JP | H06-237993 A | 8/1994 |
| JP | 2012-524626 A | 10/2012 |
| JP | 2013-017899 A | 1/2013 |
| JP | 2014-061438 A | 4/2014 |
| WO | WO 2006/116603 | 11/2006 |
| WO | WO 2010/040819 | 4/2010 |
| WO | WO 2010/124087 | 10/2010 |
| WO | WO 2016/026525 | 2/2016 |

OTHER PUBLICATIONS

Intellectual Property Office, GB Search Report for application No. GB1611409.2 dated Dec. 21, 2016 (3 pages).

Japanese Patent Office, Office action for application JP 2018-568318, dated Apr. 13, 2021, with English translation attached (10 pages).

Japanese Patent Office, Office Action dated Aug. 24, 2021 for Japanese Patent Application No. 2018-568318 (2 pages).

Japanese Patent Office, English translation of Office Action dated Aug. 24, 2021 for Japanese Patent Application No. 2018-568318 (2 pages).

* cited by examiner

PERFUSION SYSTEM WITH HEAT EXCHANGER

This is a continuation of U.S. patent application Ser. No. 16/311,938, which is a national stage application of PCT/GB 2017/051898, filed Jun. 29, 2017, and claims the benefit of United Kingdom patent application number 1611409.2, filed Jun. 30, 2016, United Kingdom patent application number 1706563.2, filed Apr. 25, 2017, and United Kingdom patent application number 1707935.1, filed May 17, 2017, the full disclosures of which are incorporated by reference herein.

FIELD OF THE INVENTION

The present invention relates to a heat exchange mechanism for use with extracorporeal fluids, such as in a blood supply system. In particular, the present invention relates to methods and systems for controlling the temperature of a fluid passing a treatment device of an extracorporeal perfusion system. This may be used to control the temperature of blood in an extracorporeal oxygenator or of the cardioplegia carrier fluid in a cardioplegia pump.

BACKGROUND

During surgical procedures, heater-cooler systems are used to set the temperature of extracorporeally circulating fluids before they are returned to a patient. During surgery, for instance, a patient's body may be cooled by induced hypothermia to as low as perhaps 15 degrees Celsius, below the normal body temperature of 37 degrees Celsius, to reduce metabolic activity. Conversely, other parts of the body, such as an isolated limb or the peritoneal cavity, may be selectively warmed to a temperature exceeding 37 degrees, or less than 37 degrees.

Conventional heater-cooler systems comprise one or more water baths to supply temperature-controlled water as a heater-cooler transfer medium through a medical device, such as through an extracorporeal oxygenator, through a cardioplegia unit ("cardioplegic" meaning heartbeat-suppressing), or through a stand-alone heat exchanger, in order to control the temperature of fluid administered to a patient. For instance, oxygenators comprise a heat exchange mechanism with connectors for receiving temperature-controlled water as a heat transfer medium from the heater-cooler system, to set the temperature of blood oxygenated in an oxygenator so that the temperature is suitable for subsequent administration to a patient. Similarly, cardioplegia, isolated limb perfusion, left-heart bypass, and other procedures use heat exchangers to control blood temperature.

The present invention is concerned with improving the temperature management during surgical procedures.

SUMMARY OF THE INVENTION

In accordance with a first aspect of the invention, there is provided a method of controlling thermal transfer in a perfusion system heat exchanger of an extracorporeal fluid treatment device, wherein the extracorporeal fluid treatment device is a device for conditioning an extracorporeal patient fluid for administration to a patient. The method comprises the steps of providing a perfusion system heat exchanger, wherein the perfusion system heat exchanger comprises a first fluid passage for a liquid heat transfer medium and a second fluid passage for the extracorporeal patient fluid to be temperature-controlled via exchange of thermal energy with the heat transfer medium, and providing the heat transfer medium through the first fluid passage, wherein the heat transfer medium comprises a component with anti-microbial properties.

The provision of antimicrobial fluid, ie a fluid with anti-microbial properties, reduces the risk of microbe contamination of the extracorporeal fluid, and hence the risk of clinical complications.

Advantageously, the provision of antimicrobial fluid reduces the requirement for time-consuming manual sterilisation procedures.

WO2006/116603A2 discloses a heat exchange catheter to regulate the temperature of a patient or a region of a patient's body by providing a source of cooling or heating fluid for circulation within the catheter. In WO/2006116603A2 it is suggested that, instead of a catheter, the heating fluid may be circulated through a heating or cooling pad or blanket designed to be used externally on a patient.

A system as that described in WO2006/116603A2 is used to indirectly control a temperature of a body or body region. The present invention departs from what was done before by using an antimicrobial fluid in direct thermal exchange with an extracorporeal patient fluid. As set out below in this specification, by "extracorporeal patient fluid", a fluid to be temperature-controlled for administration into a patient is meant, in particular for administration into the vascular system of a human patient, where it mixes with blood and comes into direct contact with organs.

An extracorporeal patient fluid may be, for instance, blood, saline, or a carrier fluid for a medical substance (eg to control anti-coagulation or heart beat). Because an extracorporeal patient fluid is intended for administration into a patient, its processing is subject to stringent safety procedures. Various properties of the extracorporeal patient fluid are conditioned within narrow safety margins. To provide an indication of the properties that may be conditioned, these may include flow rate, pressure, acidity (pH), composition (e.g. diluted or enriched with platelets) etc. The extracorporeal patient fluid needs to be sterile and its composition is controlled strictly to avoid harm and to avoid complex interaction between substances, as complex interactions may lead to unintended consequences. One of the properties to be controlled within narrow safety margins may be temperature.

A heat exchanger for other clinical devices is distinguished from an extracorporeal fluid treatment device in that extracorporeal fluid treatment devices have, historically, only been approved for use with water. As an example, oxygenators or cardioplegia units with heat exchangers will only be approved for use with water. As a consequence, manufacturers have only considered water as a heat exchange medium.

The present applicant has appreciated that the use of anti-microbial components has several benefits. One benefit is that this reduces the risk of contamination. A further benefit is that sterilization requirements of other components that may be used to manage thermal exchange with the heat transfer fluid can be subject to less stringent sterility requirements. This in turn allows components to be used that may have preferable heat exchange properties.

The benefit of the invention is therefore not necessarily related to a treatment of the human or animal body as such. One interest is reducing the risk of microbial contamination. Another interest is optimising heat transfer properties of the heat transfer medium side of a perfusion system heat exchanger. This has advantages in energy management, particularly in devices or operating modes relying on back-up power (eg battery) during emergency situations. To provide context, perfusions systems may be provided in the form of integrated perfusion systems comprising multiple components on a single trolley. The trolley may carry an input interface, blood and gas processing units, a blood reservoir, several pumps, and a battery backup system to allow the system to operate during a power failure, either to continue treatment or to ensure a controlled shut down. Heating/cooling operations are power consuming and any energy saving is critical.

It is in this context that the use of a heat transfer medium in the first fluid passage of an extracorporeal fluid treatment device is particularly beneficial.

In some embodiments, the perfusion system heat exchanger is part of an oxygenator.

In some embodiments, the perfusion system heat exchanger is part of a cardioplegic agent delivery system.

In some embodiments, the perfusion system heat exchanger is provided to control the temperature of an extracorporeal patient fluid in a fluid line.

The perfusion system heat exchanger may be a 'stand-alone' heat exchanger that can be configured to control the temperature of a fluid in a particular section of tubing.

In some embodiments, the method comprises a step of ensuring that the first fluid passage is fluidically isolated from the second fluid passage.

Passing a fluid with anti-microbial properties through a treatment device for extracorporeal fluid that is intended for administration to a patient carries an increased risk that, in the case of material failure, the heat transfer fluid may leak into the extracorporeal patient fluid.

The step of ensuring that the first fluid passage is fluidically isolated from the second fluid passage may comprise a visual inspection, for instance, to provide reassurance that no structural damage is present.

The step of ensuring the fluidic isolation of the first and second fluid passages may be carried out repeatedly.

The step of ensuring fluidic isolation of the first and second fluid passages may be implemented by providing a fluid passage from a more robust material. For instance, typical oxygenators are made from plastic and the components of the oxygenator, including its housing and heat exchange passages, may be moulded from the same material. As a departure from how typical oxygenators are used, the step of ensuring fluidic isolation may include providing the first fluid passage and/or the second fluid passage from a material comprising or consisting of metal. The metal may be steel, in particular stainless steel. The invention may therefore be provided in the form of an oxygenator comprising a metal (eg stainless steel) heat exchange fluid passage.

In some embodiments, the heat transfer medium is heater-cooler fluid.

The heat transfer medium may be heater-cooler fluid provided by a heater-cooler device. Exemplary heater-cooler devices are described below.

In some embodiments, the heat transfer medium has biocidal properties.

In some embodiments, the heat transfer medium heat transfer medium comprises glycol, in particular ethylene glycol and/or propylene glycol.

For instance, in some embodiments, the invention provides using glycol provided by a heater-cooler as a heat transfer medium directly into the heat exchanger of an oxygenator and/or of an cardioplegia unit.

In some embodiments, the perfusion system heat exchanger is part of a system capable of operating at sub-atmospheric pressure.

The method may comprise operating the perfusion system heat exchanger at sub-atmospheric conditions. For instance, an oxygenator may be operated at sub-atmospheric pressure in order to provide hypobaric oxygenation. Reasons for operating an oxygenator in this manner are described below.

In accordance with a second aspect of the invention, there is provided a heater-cooler apparatus for a perfusion system heat exchanger as defined in claim 12. The heater-cooler apparatus comprises a heater cooler device and antimicrobial fluid. The antimicrobial fluid may be thermal transfer fluid.

The provision of antimicrobial fluid reduces the risk of microbe contamination of an extracorporeal fluid, and hence the risk of clinical complications.

Advantageously, the provision of antimicrobial fluid reduces the requirement for time-consuming manual sterilisation procedures.

By "antimicrobial" it will be understood that the fluid retards microbial growth, for example, the fluid retards the growth of one or more bacteria, viruses or fungi.

It will be understood that "retards microbial growth" refers to the killing of microbes (biocidal) and/or the inhibition or complete prevention of microbe growth (biostatic).

Thus, in embodiments the antimicrobial fluid is biocidal.

In embodiments the antimicrobial fluid is biostatic.

In some embodiments, the heater-cooler fluid is constituted by the antimicrobial fluid.

In some embodiments, the heater-cooler apparatus further comprises an intermediate heat exchanger between the heater-cooler device and an intermediate passage, wherein the heater-cooler device is provided to supply heater-cooler fluid to the intermediate heat exchanger, the intermediate passage is provided for an intermediate fluid to be supplied to the perfusion system heat exchanger, and wherein the intermediate heat exchanger permits heat exchange between the heater-cooler fluid and the intermediate fluid, whereby the heater-cooler fluid is fluidically isolated from the perfusion system heat exchanger.

In some embodiments, the intermediate fluid is constituted by the antimicrobial fluid.

In some embodiments, the antimicrobial fluid is used as both heater-cooler fluid and intermediate fluid. This further reduces the risk of microbe contamination of an extracorporeal fluid.

In some embodiments, fluid provided by the heater-cooler apparatus consists of antimicrobial fluid.

In some embodiments, the antimicrobial fluid is biostatic. In some embodiments, the antimicrobial fluid is biocidal.

The antimicrobial fluid may comprise one or more antimicrobial additive(s). The one or more antimicrobial additive(s) may be biocidal.

The antimicrobial fluid may comprise glycol. Glycol can act as an antimicrobial agent and advantageously also functions as an anti-freeze agent. This provides improved thermal properties to the antimicrobial fluid.

In some embodiments, the glycol comprises propylene glycol.

Other suitable anti-freeze compounds will be known to the skilled person; one or more of the suitable anti-freeze compounds may be used in combination with or instead of glycol.

In some embodiments, the antimicrobial fluid comprises water and/or brine.

The antimicrobial fluid may comprise one or more anti-corrosion additives.

In some embodiments, the antimicrobial fluid comprises water and glycol.

In some embodiments, the antimicrobial fluid comprises or consists of water, glycol and antimicrobial additives.

In some embodiments, the antimicrobial fluid comprises or consists of water, glycol, antimicrobial additives and anti-corrosion additives.

Any embodiments of the second aspect may be combined with embodiments of the first aspect. The heater cooler apparatus may be used to provide the anti-microbial fluid used in embodiments of the first aspect. For instance, the heater cooler apparatus may be used to provide glycol as thermal transfer fluid to an oxygenator and/or to a cardioplegic agent delivery system. The same heater cooler apparatus may be used to supply thermal transfer fluid to multiple perfusions system heat exchangers.

According to a third aspect of the invention, there is provided use of an antimicrobial fluid as thermal transfer fluid in an extra-corporeal perfusion system as defined by claim 20.

According to a fourth aspect of the invention, there is provided a heater-cooler apparatus for a perfusion system heat exchanger as set forth in claim 21. The apparatus comprises an intermediate heat exchanger between a heater-cooler device and an intermediate passage, wherein the heater-cooler device is provided to supply heater-cooler fluid to the intermediate heat exchanger, the intermediate passage is provided for an intermediate fluid to be supplied to the perfusion system heat exchanger, and wherein the intermediate heat exchanger permits heat exchange between the heater-cooler fluid and the intermediate fluid, whereby the heater-cooler fluid is fluidically isolated from the perfusion system heat exchanger.

It will be understood that a heater-cooler device typically comprises a tank for a heat transfer fluid, a heater for heating the heat transfer fluid and/or a cooler for cooling the heat transfer fluid, a supply port for providing heat transfer fluid for a perfusion system heat exchanger, and a return port for receiving heat transfer fluid back into the heater-cooler device.

The perfusion system heat exchanger may be used in combination with a treatment device, such as a blood processing device in which blood is processed in the course of extracorporeal perfusion. Examples for a blood processing device include an extracorporeal oxygenator and a cardioplegic agent delivery system. Blood processing devices are used to prepare blood or other liquids for administration to a patient.

Preparing includes setting the fluid properties, such as temperature, driving pressure, and flow rate, so that these are suitable for subsequent administration to a patient. The heat exchanger may be integral with the treatment device or positioned separately, as a stand-alone heat exchanger, e.g., downstream of a treatment device.

Conventionally, the heater-cooler fluid is supplied at a controlled temperature to a perfusion system heat exchanger, which may be the heat exchanger of an oxygenator line or a cardioplegia line, or of any other component of a perfusion system. This is to set the temperature of the fluid passing through the oxygenator line or the cardioplegia line. Heater-cooler fluid may also be provided to a temperature-control mat to help maintaining a predefined patient body temperature.

By providing an intermediate passage that is fluidically isolated from the heater-cooler fluid, an intermediate fluid other than the heater-cooler fluid can be provided in the intermediate passage. The heater-cooler fluid and the intermediate fluid may be different substances. This allows heat exchange via the intermediate heat exchanger between the heater-cooler fluid and the intermediate fluid. The intermediate fluid can be circulated through the perfusion system heat exchanger, without bringing the perfusion system heat exchanger, or components of the perfusion system heat exchanger such as coils, into contact with the heater-cooler fluid.

This provides an advantage over using water as a heater-cooler fluid. Warmed water has been shown to foster growth of potentially harmful organisms. Although fluidically isolated from the blood in the perfusion system, it is believed that droplet cross-contamination from the heater-cooler water baths may lead to, or contribute to, clinical complications.

Sterilisation of heater-cooler devices is time-consuming, as it involves manually wiping every part and connector, and repeatedly rinsing, heating, and flushing tanks with antiseptics in a procedure that can take in the region of a few hours. Further, manual sterilisation procedures carry the potential of damaging a heater-cooler device. Also, there is a risk of sterilisation procedures not being sufficiently effective.

To better address this problem, it has been investigated to use fluids that retard microbial growth (which may be referred to as antiseptic or antimicrobial fluids), as an alternative to water as the heater-cooler fluid. As an example, propylene glycol may be used as heater-cooler fluid. Propylene glycol has antimicrobial properties. Alternatively, ethylene glycol may be used as heater-cooler fluid. Some organisms can live in ethylene glycol, and so additional antimicrobial agents may be added.

Since existing perfusion system apparatus, such as extra-corporeal blood oxygenators and cardioplegic agent delivery devices, use water as the heat transfer medium, existing systems have only been approved by the relevant regulatory body for use with water. This has also meant that the heater-cooler systems that are used to supply the heat transfer media to the perfusion system apparatus only provide water. There has thus been no incentive, nor any consideration of the skilled person to consider other transfer media. Practically available antiseptic fluids are also often corrosive and damaging to heat exchanger coils of the perfusion system device, reducing the lifetime of perfusion system heat exchangers.

The provision of an intermediate passage allows an antiseptic fluid, e.g. propylene glycol, to be used in the heater-cooler bath, while using less corrosive fluids, e.g. water, or sterilised water, in the intermediate passage. This reduces the risk of cross-contamination originating from the heater-cooler bath, while helping to conserve components of perfusion system devices such as the heat exchange coils.

In some embodiments, the intermediate fluid is antimicrobial fluid. In some embodiments, the heater-cooler fluid is antimicrobial fluid. In some embodiments, the intermediate fluid and the heater-cooler fluid are antimicrobial fluid.

Because the intermediate passage is fluidically isolated and the intermediate fluid can be circulated through the perfusion system heat exchanger and the intermediate heat exchanger in a closed loop, this means that, in some embodiments, the circuit of the intermediate passage can be constructed as a one-use or disposable unit. This means that possible longer-term, corrosive effects of the fluid need not be a concern.

In some embodiments, the intermediate heat exchanger is integral with the intermediate passage.

This facilitates the installation, exchange and/or removal of an intermediate passage and a corresponding intermediate heat exchanger. For instance, this allows ensuring that an appropriately dimensioned heat exchanger is used for the intermediate passage. It will be understood that the intermediate passage may be constituted by a conduit of the intermediate heat exchanger.

In some embodiments, the intermediate heat exchanger comprises a first heat exchange element for integration with the heater-cooler device and a second heat exchange element integral with the intermediate passage.

The first heat exchange element and the second heat exchange element can be connected, to thermally couple, to make up a heat exchanging arrangement. For instance, the first heat exchange element may be constituted by a first radiator plate, and the second heat exchange element by a second radiator plate, that can be coupled to permit heat exchange between the plates.

In some embodiments, the intermediate heat exchanger and/or the intermediate passage is detachable from the heater-cooler device.

A detachable intermediate passage can be used as a disposable, or "consumable", device. This further reduces a cross-contamination risk, as an intermediate passage may be used for a single course of treatment and then discarded. In embodiments with an integral intermediate heat exchanger or with an integral heat exchange element, this is also detachable together with the intermediate passage.

It is understood that, by "detachable", it is meant that the intermediate heat exchanger and/or intermediate passage can be attached to, and removed from, the heater-cooler device without damaging the heater-cooler device. The intermediate heat exchanger and/or intermediate passage is thus attachable and detachable.

This further reduces the risk of an inadequate sterilisation procedure resulting in microbial growth, because the heater-cooler device can be operated with a sterile fluid and the intermediate passage, which is to be used with warmed water, is to be discarded after each treatment course.

After disposal of a used intermediate heat exchanger and/or intermediate passage, a replacement can be used for a subsequent procedure, while the sterilisation requirements for the heater-cooler device are reduced. Thus, the provision of a disposable device further reduces the risk of microbial growth.

In some embodiments, an intermediate heat exchanger and/or intermediate passage that is detachable comprises an arrangement preventing re-attachment to a heater-cooler device.

The arrangement preventing re-attachment may be embodied by a mechanism that breaks an integral component of the intermediate passage.

For instance, a consumable intermediate passage may comprise a connecting mechanism that permits a single attachment to a heater-cooler device and that alters its configuration upon attaching or detaching such that once detached, the same connecting mechanism cannot be re-attached. To this effect, the connecting mechanism may comprise a collapsible element or a feature of pre-determined weakness constituting a feature for altering the configuration.

The re-attachment preventing arrangement prevents the unintentional re-use of a used device and thereby reduces a contamination risk.

The intermediate passage may comprise a tag, such as an RFID tag with unique serial number. The heater-cooler system may have an interface for communicating with the RFID tag. This may be used to store information relevant to the use of the intermediate passage.

For instance, a controller of the heater-cooler apparatus may store information on the use of intermediate passages with the heater-cooler device. The heater-cooler apparatus may comprise a configuration to deny use of an intermediate passage that is identified as having been used before. The heater-cooler apparatus may issue a notification if an intermediate passage is used longer than a pre-indicated amount of time. For instance, the heater-cooler apparatus may be configured to issue a notification signal if an intermediate passage has been in use for over 20 hours.

Likewise, a controller or memory device associated with the intermediate passage may be configured to store information on the use of the intermediate passage.

In some embodiments, the intermediate heat exchanger and/or intermediate passage comprises a quick-connect mechanism for fluid connection with the heater-cooler device and/or for fluid connection with the perfusion system heat exchanger.

This facilitates installation of the intermediate passage between the heater-cooler device and the perfusion system heat exchanger. By quick-connect mechanism, a mechanism is meant that allows fluid-tight connection to be established by a push-fit or push-turn fit that can be effected with one, or only a few hand movements. For instance, the quick-connect mechanism may be a Hansen-style quick connect coupling, or similar.

In some embodiments, the quick-connect mechanism comprises or is constituted by a self-sealing membrane.

This facilitates the installation of the device while providing a fluid-tight connection.

In some embodiments, the heater-cooler apparatus comprises a flow-control arrangement for controlling the flow rate of either or both of the heater-cooler fluid and the intermediate fluid.

Control of the flow rate of either or both of the heater-cooler fluid and the intermediate fluid allows the heat exchange between the heater-cooler fluid and the intermediate fluid to be improved. The flow control arrangement may be integral with the intermediate heat exchanger and/or integral with the intermediate passage.

In some embodiments, the flow-control arrangement comprises a roller pump, a centrifugal pump, or a centrifuge impeller arrangement for use with an external drive.

A roller pump, or peristaltic pump, allows pumping without contacting the fluid, and is practical for flow rates up to 7 or 8 litres per minute. In conjunction with disposable intermediate passages, the same roller pump can be used for different disposable passages. Thus, disposable systems may comprise a tubing section of sufficient length and flexibility for use with a roller pump.

Centrifugal pumps allow higher flow rates and have a higher potential flow output compared to a roller pump in a standard configuration. Centrifugal pumps may be integrated with a disposable system. Likewise, an axial flow pump, a finger pump, or a M-type pump may be used.

The intermediate passage may comprise an integrated impeller. The integrated impeller may comprise a magnet. The magnet may be overmoulded so as to be fluidically isolated.

The impeller may be used as a centrifuge impeller for use with an external drive mechanism. For instance, the intermediate passage may comprise an integrated magnetic impeller for use with an external magnetic impeller drive.

By providing a flow-rate control mechanism, a more energy-efficient mode of operation may be implemented, because the heat exchange can be better modulated by the controlling the flow rate of one fluid relative to the other fluid.

In some embodiments, the heater-cooler apparatus comprises one or more non-return valves in the intermediate passage or in a heater-cooler conduit supplying the heater-cooler fluid.

A non-return valve may be positioned near or at a connector of the intermediate heat exchanger or the intermediate passage. This helps to contain heater-cooler fluid or intermediate fluid in the intermediate heat exchanger and/or in the intermediate passage after removal. This reduces the risk of spilling heater-cooler fluid, which may have corrosive properties, and/or the risk of spilling intermediate fluid, respectively, which may not be sterile.

The non-return valve may be embodied by a ball sealing valve.

In some embodiments, the heater-cooler apparatus comprises a flow sensor arrangement for determining the flow rate of the heater-cooler fluid, of the intermediate fluid, and/or an extracorporeal patient fluid passing through the perfusion system heat exchanger.

By "extracorporeal patient fluid", the fluid to be temperature-controlled for administration to the patient is meant. This may be, for instance, blood, saline, or a carrier fluid.

The flow sensor arrangement allows the actual flow rate of the heater-cooler fluid, the intermediate fluid, and/or the extracorporeal patient fluid to be determined. This provides a better degree of feedback of the actual flow rate of the respective fluids, which can be used to control the flow rates of one or more of the respective fluids in response to the actual flow rate.

The flow sensor arrangement may be constituted by an arrangement deriving the flow value from the operational parameters of the flow-controlling arrangement. E.g., for a given setup using a pump to control the flow rate, (e.g., pump speed, tube diameter, etc.), the revolutions, or strokes, per minute can be correlated with the flow rate. For instance, the flow sensor arrangement may be constituted by an arrangement deriving operational parameters from an external motor used to drive a centrifuge impeller.

This allows a feedback control loop to be implemented. For instance, an example of an extracorporeal patient fluid is oxygenated blood to be returned to a patient. To provide an illustrative example, it may be necessary for clinical reasons to increase the supply of oxygenated blood to a patient. In other words, the flow rate of the extracorporeal patient fluid may be increased, and therefore also the flow rate through the heat exchanger of the oxygenator. In that case, the perfusion system heat exchanger may require an adequate supply of temperature-controlled intermediate heat transfer fluid. This may be ensured by a closed loop control ensuring an appropriate temperature gradient by setting an appropriate flow rate and/or temperature.

By being able to determine and control the heat transfer requirements, more efficient heat transfer procedures can be implemented.

In embodiments, the heater-cooler apparatus comprises a temperature sensor arrangement for determining the temperature of the heater-cooler fluid, of the intermediate fluid, and/or an extracorporeal patient fluid passing through the perfusion system heat exchanger.

This allows a feedback control loop to be implemented. For instance, a controller may interpret the temperature value, as read by a temperature sensor of the temperature sensor arrangement, against a set temperature threshold. The controller may operate the flow-control arrangement to reduce or increase, as necessary, the rate at which temperature-controlled fluid is circulated, to increase or to reduce the heat exchange rate at the perfusion system heat exchanger.

The temperature sensor may be constituted by any suitable temperature sensor, such as a thermistor probe, which could rest in a well in a heat exchange circuit. Another option is an infrared temperature sensor which is suitable for indirect measurements of fluid in a line. Non-contact sensors may be used to measure the temperature inside a disposable intermediate passage.

In some embodiments, the intermediate passage comprises a fill port.

A fill port facilitates the filling and emptying of the intermediate passage before and after use. The port may comprise a connector for tubing, to facilitate a fluid tight connection for filling and emptying. The fill port may be constituted by a suction system, provided to aspire fluid from a container, and to concomitantly vent air displaced by the fluid.

In accordance with a fifth aspect of the invention, there is provided a heat transfer device for circulating an intermediate fluid as a heat transfer medium between a heater-cooler fluid and a perfusion system heat exchanger, as defined in claim 36. The heat transfer device comprises a first conduit and a heat exchange element. The first conduit comprises attachments for connection to a heat exchanger inlet and to a heat exchanger outlet of the perfusion system heat exchanger to form an intermediate passage for the intermediate fluid through the perfusion system heat exchanger and through the heat exchange element. The heat exchange element is configured to permit heat transfer between the heater-cooler fluid and the intermediate fluid, while fluidically isolating the heater-cooler fluid from the intermediate fluid and from the perfusion system heat exchanger.

In some embodiments, the intermediate fluid is an antimicrobial fluid.

In some embodiments, the heater-cooler fluid is an antimicrobial fluid.

In some embodiments, the heat exchange element comprises a second conduit, the second conduit connectable to the supply port and to the return port of a heater-cooler device.

In some embodiments, the heat exchange element is configured for coupling with a heat exchanger plate that is attached to the supply port and the return port of a heater-cooler device.

In some embodiments, the heat transfer device further comprises a quick-connect mechanism for fluid connection with the heater-cooler device and/or for fluid connection with the perfusion system heat exchanger.

In some embodiments, one or more connectors comprise an arrangement preventing re-attachment.

In some embodiments, the heat transfer device further comprises one or more non-return valves in the first conduit and/or in the second conduit.

In some embodiments, the heat transfer device further comprises or an impeller arrangement for use with an external drive.

In some embodiments, the heat transfer device further comprises a fill port.

It will be understood that the heat transfer device of the third aspect may be used to form the intermediate heat exchanger and/or the intermediate passage of the second aspect. Thus, embodiments of the third aspect may comprise one or more features described in relation to the intermediate components in any one of the embodiments of the second aspect. For instance, the first conduit may comprise a fill port. The first conduit may comprise a flow-control arrangement. For instance, the flow-control arrangement may comprise an integral pump. The flow-control arrangement may comprise an integral impeller for use, together with an external drive mechanism, as an impeller of a centrifugal pump. The impeller may be magnetic (or coupled with a magnet) for use with an external magnetic drive mechanism. The flow-control arrangement may be constituted by a section of sufficient length for use with a roller pump.

In accordance with a sixth aspect of the invention, there is provided a method of setting the temperature of an extracorporeal fluid passing through a perfusion system heat exchanger, as defined in claim 47.

The method comprises the steps of the method comprising the steps of providing a heater-cooler device, providing heater-cooler fluid in the heater-cooler device, providing an intermediate passage between the heater-cooler device and the perfusion system heat exchanger, providing an intermediate fluid in the intermediate passage, arranging for a heat exchange between the heater-cooler fluid and the intermediate fluid while fluidically isolating the intermediate fluid from the heater-cooler fluid, and supplying the intermediate fluid to the perfusion system heat exchanger for controlling the temperature of the extracorporeal fluid through the perfusion system heat exchanger.

In some embodiments, the heater-cooler fluid to be provided in the heater-cooler device is a fluid with stronger antiseptic properties than water.

In some embodiments, the heater-cooler fluid to be provided in the heater-cooler device is antimicrobial fluid.

In some embodiments, the intermediate fluid to be provided in the intermediate passage is water.

In some embodiments, the intermediate fluid to be provided in the intermediate passage is antimicrobial fluid.

In some embodiments, the step of providing the intermediate passage comprises the step of connecting a first conduit to the inlet and the outlet of the perfusion system heat exchanger to form the intermediate passage through the perfusion system heat exchanger.

In some embodiments, arranging a heat transfer between the heater-cooler fluid and the intermediate fluid comprises the step of connecting a second conduit to the supply port and to the return port of the heater-cooler device to form a passage through a heat exchange element.

In some embodiments, the step of providing the intermediate passage comprises the step of coupling a heat exchange element of the intermediate passage with a heat exchanger plate that is attached to a supply port and to a return port of the heater-cooler device.

In some embodiments, the method comprises determining one or more of the flow rate and the temperature of the heater-cooler fluid, of the intermediate fluid, and/or the extracorporeal fluid passing through the perfusion system heat exchanger.

In some embodiments, the method comprises controlling the flow rate of the heater-cooler fluid and/or the intermediate fluid.

The method in accordance with the sixth aspect may involve the use of any one of the embodiments of the first to fifth aspects. For instance, in embodiments the method may involve replacing a used intermediate heat exchanger with an unused intermediate heat exchanger. Such a replacement may be carried out between two treatment procedures.

In embodiments of the aspects described above, the perfusion system heat exchanger may be incorporated in an oxygenator. The oxygenator is provided to oxygenate oxygen-reduced (venous) blood by exposure to an oxygenation supply gas, and unused oxygenation gas is removed as exhaust gas via a gas outlet of the oxygenator.

The oxygenator may be a closed system, by which is meant that the gas pathways for the oxygenation gas between the oxygenator inlet and the oxygenator exhaust are pressure-isolated from the atmosphere outside of the oxygenator. As such, the pressure inside the oxygenator from a supply gas inlet to an exhaust gas outlet may be maintained below atmospheric pressure. This may be achieved by using a low pressure source to effect a flow out of the exhaust gas outlet. A closed system allows sub-atmospheric pressure levels in the oxygenator while the outside of the oxygenator can be expected to be at ambient pressure.

Even though operable as a closed system, an oxygenator may require a fail-safe mechanism against over-pressurisation (e.g. due to accidental blocking of an exhaust gas tube while oxygenation gas continues to be supplied at the supply gas inlet). For instance, Great British patent application GB1705556.7 by the present applicant discloses a pressure-isolation device and method that pressure-isolates an oxygenator exhaust chamber from the environment outside the oxygenator in order to allow oxygenation to be performed in closed-system conditions and, thus, at sub-atmospheric pressures. The pressure isolation device described in GB1705556.7 provides a fail-safe mechanism against over-pressurisation of the exhaust gas chamber.

Oxygenation at sub-atmospheric pressure, or hypobaric oxygenation is of interest for reasons set out below. To better appreciate hypobaric oxygenation, a summary of relevant mechanism taking place during routine atmospheric oxygenation is provided, using the example of a hollow fibre oxygenator. Oxygenation gas (ie gas that is similar to air and mixed to a required oxygen and nitrogen content in order to achieve a desired partial pressure of oxygen and partial pressure of carbon dioxide in the arterial blood) is directed via a tube and, if required, also through an anaesthetic agent vaporizer, to the gas inlet of the oxygenator, and through the bundle of hollow fibres (the gas phase), while blood is passed inside the oxygenator over the outside (the blood phase) of the hollow fibres. The fibre walls are gas-permeable and gas transfer occurs via the fibre walls due to the diffusion gradient from higher concentration (eg of oxygen in the oxygenation gas, or of carbon dioxide in the venous blood) to lower concentration (eg of oxygen in the venous blood, or of carbon dioxide in the oxygenation gas).

The blood exiting the oxygenator is referred to as arterial blood and is oxygenated to have a required partial pressure of oxygen on the arterial blood (PaO2) and a required partial pressure of carbon dioxide in the arterial blood (PaCO2). PaO2 and PaCO2 are adjusted as follows. PaO2 can be influenced by adjusting by the oxygen content of the oxygenation gas (Fraction of Inspired Oxygen, FiO2), relative to the fraction of nitrogen in the oxygenation gas (FiN2). Most of the blended air consists of nitrogen. PaCO2 can be influenced by adjusting the flow rate (commonly referred to as "Sweep") of the oxygenation gas. Nitrogen in the gas phase seeks to balance itself to be equal in pressure in the gas phase compared to the blood phase.

A problem with extracorporeal oxygenation systems exists with the risk of formation of gaseous microemboli bubbles (GME) which may be propelled through the blood into the circulatory system, especially when the GME bubble has a high nitrogen content. Nitrogen-containing GME are produced when air comes into contact with blood. There are many opportunities for this to happen in a clinical scenario, eg when air and blood mix during blood suction, in open cardiac chambers, during certain drug administration procedures, during high negative pressure areas in the pump circuit, or during warming when the temperature of the blood does not allow the current volume of nitrogen to stay dissolved in solution (and nitrogen thereby "comes out of solution" in the form of bubbles).

Once in the blood stream, there often is little to no diffusion gradient between a nitrogen-containing bubble in the body and surrounding blood/tissues. Thus, a nitrogen-containing bubble, once present, tends not to dissolve into solution. GME in the blood cause proteins to stick to the bubble surfaces and relatively quickly develop a coating, which acts as a barrier further inhibiting diffusion of gases into/out of the bubble. This nitrogen-containing, protein-coated bubble then behaves much like a hollow particle with a solid surface, with the same potential morbidities associated with it as are associated with solid embolus obstruction of blood flow to the tissues. Additionally, GME can harm intimal vessel layers, leading to blood vessel inflammation. This also stimulates the coagulation pathways, which can lead to bleeding/clotting problems.

Attempts to decrease GME during extracorporeal ventilation include several techniques, such as limiting blood temperature differentials, minimizing blood suction return directly to the circuit, operating any drug injection into the blood at slow rates, flooding the operative field with CO2, utilization of de-foaming chemicals in the venous/cardiotomy filters/reservoir, and arterial bubble trap/purge devices. Despite these attempts, presence of GME, as measured by sensitive instruments, is a common event in the arterial blood in extracorporeal systems.

As set out above, nitrogen is used in the oxygenation gas to set the partial pressure of oxygen in the oxygenation gas (FiO2), which, in turn, directly influences the partial pressure of oxygen in the arterial blood (PaO2) exiting the oxygenator.

By reducing or eliminating nitrogen in the oxygenation gas, eg by using pure oxygen (or a mix of oxygen and carbon dioxide), the partial pressure of nitrogen in the blood can be greatly decreased, even to the point of practical elimination. To illustrate this with an example, instead of an oxygen content similar to air, in the region of 20 to 21% (the remaining 79 to 80% being mostly nitrogen), the oxygen content may be close to 100% (with negligible nitrogen content) in the oxygenation gas entering the inlet of the oxygenator. However, if 100% oxygen is used at atmospheric pressure for extracorporeal blood ventilation, this will result in a very high partial pressure of oxygen in the arterial blood (PaO2). A high PaO2 is undesirable because it has adverse effects on a patient, eg due to damaging free oxygen radicals that can be produced. Furthermore, high partial pressures of gases in blood have the counterproductive effect of increasing the tendency for GME development due to the dissolution-inhibiting effect.

However, if higher oxygen content is provided at sub-atmospheric pressures, the corresponding partial pressure in the arterial blood leads to a lower oxygen content in the blood at equilibrium. As such, at sub-atmospheric pressure levels, a non-gas-saturated arterial blood environment is provided in the oxygenator, and the partial pressure of oxygen PaO2 is lower without the need to use nitrogen in the oxygenation gas.

Furthermore, in the non-gas-saturated condition, any bubbles in the blood tend to dissolve more quickly, practically before a protein coating can form on the bubble-blood interface. There is therefore believed to be a two-fold benefit of avoiding the need for nitrogen in the oxygenation gas and hypobaric ventilation: in addition to preventing GME formation, non-gas-saturated blood is also believed to promote the dissolution of existing bubbles.

The use of an anti-microbial heat transfer fluid, such a glycol, in an oxygenator with hypobaric capability allows different rates of temperature change than is possible when using water as heat transfer fluid. This allows the energy management to be improved, which is of interest when relying on backup energy, as well as providing a reduced risk of microbial contamination.

DESCRIPTION OF THE FIGURES

Exemplary embodiments of the invention will now be described with reference to the Figures, in which.

DESCRIPTION

Figure 1:
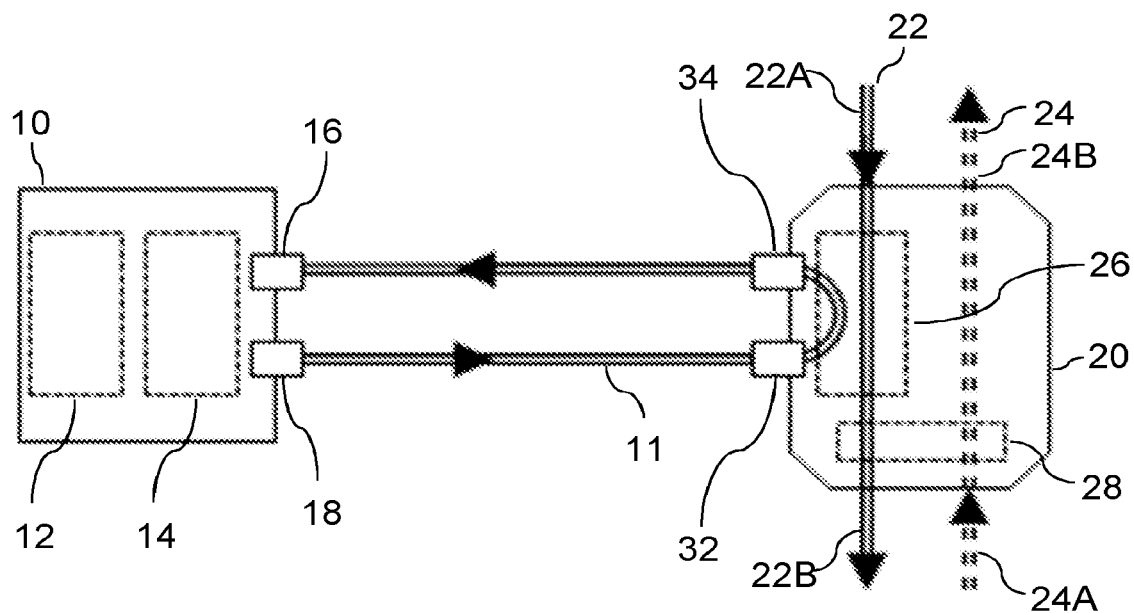
FIG. 1 shows a schematic arrangement of components of a prior art heater-cooler arrangement.

FIG. 1 shows, schematically, a prior art heater-cooler system for use with a perfusion system. The heater-cooler system comprises a heater-cooler device 10 with a heater 12 and a cooler 14. The heater 12 and the cooler 14 are used to set the temperature of a heater-cooler fluid 11. The heater-cooler fluid 11 is, via a supply port 18, circulated to a perfusion system heat exchanger, and returned to the heater-cooler device via a return port 16.

The perfusion system heat exchanger is illustrated as an integral component of an oxygenator 20. The oxygenator 20 comprises a blood line 22 which flows blood via an oxygenation membrane 28 for exposure to an oxygenation gas from an oxygen supply line 24. Before oxygenation in the oxygenator, the blood is in a condition 22A. After oxygenation, the blood leaves the oxygenator in a condition 22B. Condition 22B may be a condition in which the blood is oxygenated for administration to a patient. Oxygenation gas in the oxygen supply line 24 is supplied in a condition 24A and exits the oxygenator as exhaust gas in a condition 24B.

The oxygenator 20 comprises an integral, or associated, heat exchanger 26 positioned along the blood line 22, upstream of the oxygenation membrane 28. The heater-cooler fluid 11 is circulated from the supply port 18 into the heat exchanger 26 via an inlet 32 to set the temperature of the blood in line 22. The heater-cooler fluid 11 leaves the heat exchanger 26 via an outlet 34 and is circulated back to the heater-cooler device 10 via the return port 16.

The FIG. 1 system allows the temperature of the blood in the condition 22B to be controlled by flowing the heater-cooler fluid 11 from the heater-cooler device 10 through the heat exchanger 26, whereby the heater-cooler fluid 11 comes into contact with the heat exchanger 26.

Figure 2:
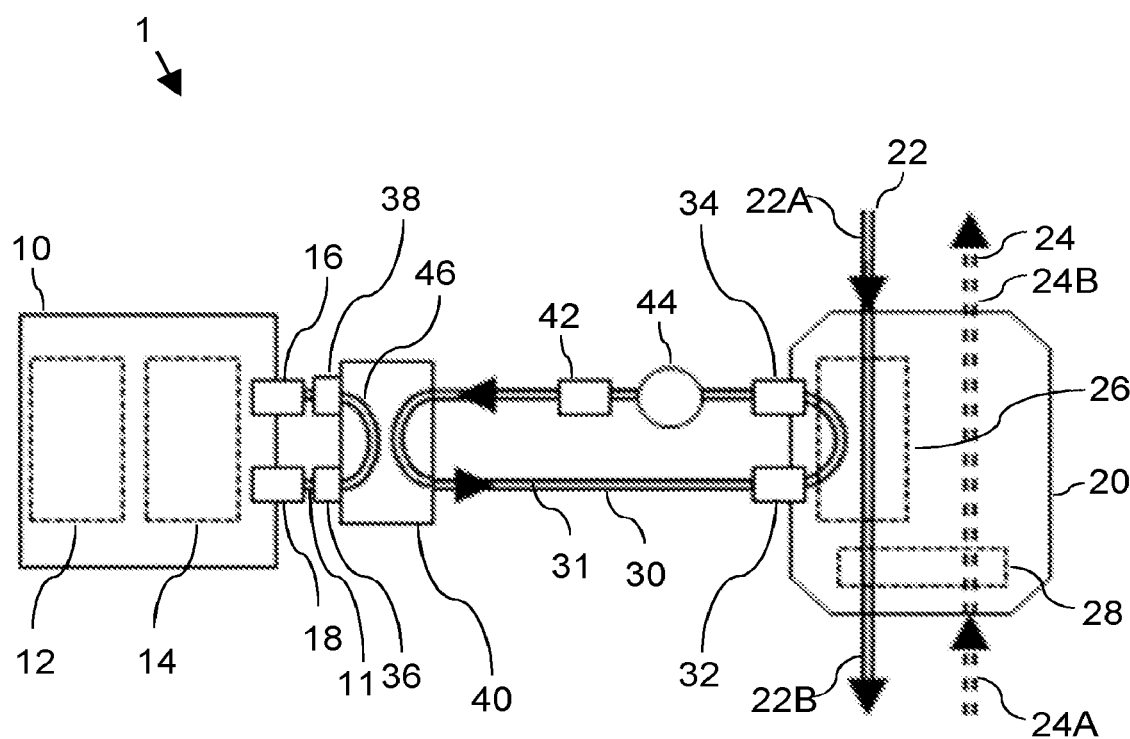
FIG. 2 shows a schematic arrangement of components of a heater-cooler apparatus in accordance with an exemplary embodiment of the present invention.
Figure 3:
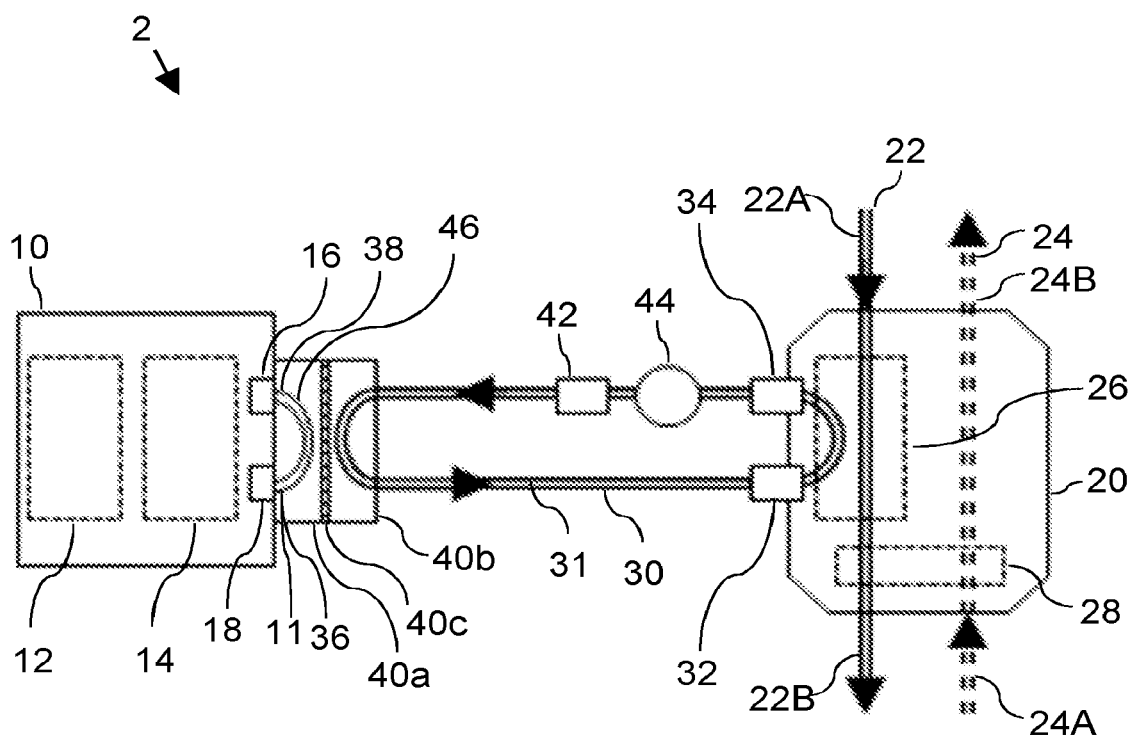
FIG. 3 shows a schematic arrangement of components of a heater-cooler apparatus in accordance with another exemplary embodiment of the present invention.

FIGS. 2 and 3 each show an exemplary embodiment of the invention. In FIGS. 2 and 3, the same numerals are used for components that correspond to those described in FIG. 1.

In FIG. 2, a heater-cooler apparatus 1 comprises a heater-cooler device 10 comprising a heater 12 and a cooler 14 which are used to set the temperature of a heater-cooler fluid 11 circulated via a supply port 18 and to be returned via a return port 16. An oxygenator 20 is provided to generate oxygenated blood 22B from oxygen-reduced blood 22A in a blood line 22 by exposure, via an oxygenation membrane 28, to oxygenation gas supplied via an oxygen supply line 24 in a condition 24A and to leave the oxygenator 20 as exhaust gas 24B.

In order to control the temperature of the blood in condition 22B to be suitable for subsequent administration to a patient, the oxygenator 20 comprises a heat exchanger 26 constituting a perfusion system heat exchanger comprising an inlet 32 for receiving a heat transfer fluid and an outlet 34 to allow heat transfer fluid to circulate away.

The system of FIG. 2 comprises an intermediate passage 30 in which an intermediate fluid 31 can be circulated. The intermediate passage 30 runs through a heat exchanger 40, which constitutes an intermediate heat exchanger of the intermediate passage. The heat exchanger 40 comprises a heater-cooler passage 46 with an entry port 36 and an exit port 38. The entry port 36 is provided for fluid connection with the supply port 18 from the heater-cooler device 10. The exit port 38 is provided for fluid connection with the return port 16 of the heater-cooler device 10.

The heater-cooler passage 46 and the intermediate passage 30 permit heat transfer between the intermediate fluid 31 and the heater-cooler fluid 11, while fluidically isolating the heater-cooler fluid 11 from the intermediate fluid 31. Thus, the heater-cooler fluid 31 may be constituted by a substance that may otherwise be harmful to the coils of the heat exchanger 26. The heat exchanger 40 may be part of a disposable system and any detrimental effect of the heater-cooler fluid 31 on the heat exchanger 40 is more tolerable than on the heat exchanger 26.

The intermediate fluid 31 is circulated through the heat exchanger 26 via the inlet 32 and the outlet 34, to control the temperature of the blood in the blood line 22.

The intermediate passage 30 comprises a pump 44 to control the flow rate of the intermediate fluid 31. The pump 44 constitutes a flow-control arrangement. The pump 44 may be controlled by a controller (not shown) and may be part of a closed-loop control system comprising a flow-sensor arrangement to maintain a set flow rate.

In addition, the intermediate passage comprises a fill port 42 to permit intermediate fluid 31 to be added and/or removed. The fill port 42 may be constituted by a suction/vent arrangement.

In FIG. 2, the fill port 42 and the pump 44 are indicated on the upper limb, downstream of the outlet 34. Either or both may be located on the lower limb, upstream of the inlet 32.

The connections of the entry port 36 and the exit port 38 may comprise quick-connect mechanisms, to facilitate installation and removal of the intermediate circuit 30. For instance, a quick-connect mechanism may comprise self-sealing membranes. The entry port 36 may be configured for attachment to the supply port 18, and the exit port 38 may be configured for attachment to the return port 16.

FIG. 3 shows an alternative embodiment in the form of a heater-cooler apparatus 2 in which the heat exchanger 40 comprises two attachable plates constituting a quick-connect mechanism. The heater-cooler device 10 is provided with a first heat exchanger plate 40a. The intermediate passage 30 comprises a second heat exchanger plate 40b. The first and second heat exchanger plates 40a and 40b can be coupled, and as shown in FIG. 3 are coupled, to make up the heat exchanger 40. The heat transfer is improved by a paste 40c applied between the plates. The use of the paste 40c is optional. Other mechanisms to improve the heat transfer between the first and second heat exchanger plates 40a and 40b may be used.

The heat exchanger 40 comprised of the first and second heat exchanger plates 40a and 40b of the FIG. 3 arrangement provides a similar fluid-isolation arrangement as that in FIG. 2: a heater-cooler passage 46 runs through the first heat exchanger plate 40a from an entry port 36 to an exit port 38. The entry port 36 is coupled with the supply port 18 of the heater-cooler device 10, and the exit port 38 is coupled with the return port 16. The coupling may be permanent, such that the first heat exchanger plate 40a is integral with the heater-cooler device 10. The intermediate passage 30 passes through the second heat exchanger plate 40b. When assembled, the intermediate fluid 31 is in thermal contact with the heater-cooler fluid 11 while being fluidically isolated.

The intermediate passage 30 may, together with the heat exchanger 40 (as shown in the FIG. 2 embodiment), or together with the second heat exchanger plate 40b (as shown in the FIG. 3 embodiment), be comprised in a disposable heat exchanger. This reduces the need for post-treatment sterilisation of the intermediate passage 30.

The description of an oxygenator 20 is exemplary for a treatment device. The heater-cooler fluid 11 may be provided to the heat exchanger of any other extracorporeal line, such as, e.g., of a cardioplegia line, or of a stand-alone heat exchanger.

The provision of a pump 44 is exemplary. Other means of controlling the flow of the intermediate fluid 31 relative to the flow rate of the heater-cooler fluid 11 may be used. The pump 44 may be constituted by a centrifugal pump that is integral with the intermediate passage 30. The pump 44 may be constituted by a centrifugal pump impeller arrangement that is integrated into the disposable system, intended to be driven by an external driver of the heater-cooler system. The integrated impeller and the external driver may be configured for magnetic coupling. Other pump types may be used, and in that case, the intermediate passage 30 may comprise tubing or characteristics that render it suitable for use with a pump type. For instance, the pump 44 may be constituted by a roller pump. The roller pump may be part of a heater-cooler control system but not part of a disposable system. To be suitable for a roller pump, the intermediate passage 30 may comprise a tubing section of sufficient length and flexibility for use with a roller pump.

The heater-cooler apparatus 1 and 2 are illustrated using a single intermediate passage 30 to supply a heat exchanger 26. The heater-cooler device 10 may be configured to simultaneously supply heater-cooler fluid for more than one heat exchanger. For instance, the heater-cooler fluid may be simultaneously supplied for an oxygenation line, a cardioplegia line, and/or a patient temperature control mat. In that case, several intermediate passages may be provided to permit simultaneous heat coupling of the intermediate passages with the heater-cooler device. For instance, two intermediate passages may be provided, one for an oxygenation line heat exchanger, and one to for a cardioplegia line heat exchanger. The heater-cooler device may be configured with a common return line from multiple intermediate passages.

Figure 4:
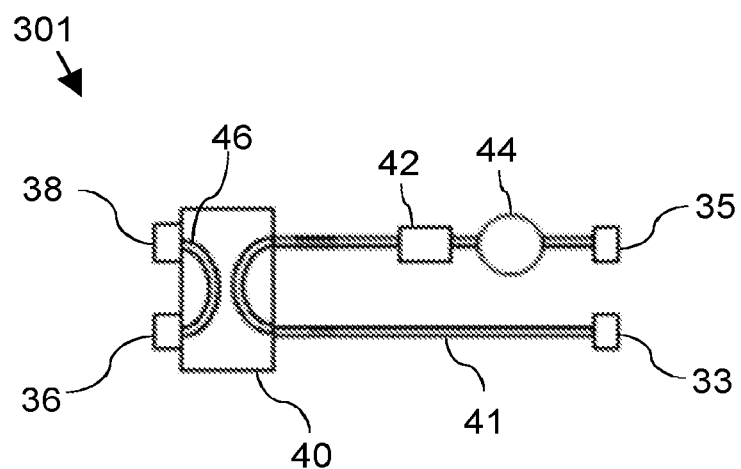
FIG. 4 shows a schematic arrangement of a heat transfer device in accordance with an exemplary embodiment of the present invention.
Figure 5:
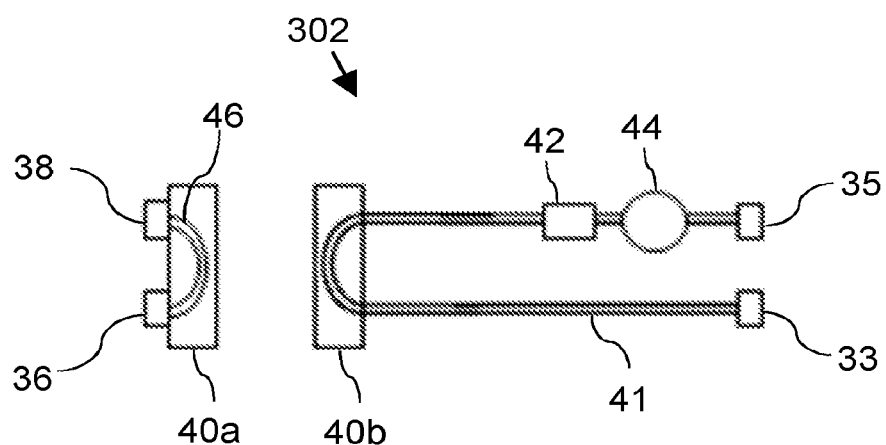
FIG. 5 shows a schematic arrangement of a heat transfer device in accordance with another exemplary embodiment of the present invention.

FIGS. 4 and 5 illustrate heat transfer devices 301 and 302, respectively, which may each be used as disposable (or "consumable") components. The heat transfer device 301 of FIG. 4 corresponds to that used in the FIG. 2 heat transfer device 1. The heat transfer device 302 of FIG. 5 corresponds to that used in the FIG. 3 heat transfer device 2.

For ease of reference, the same numerals are used in FIGS. 4 and 5 as they are used in the preceding Figures for corresponding components. The heat transfer device 301 comprises tubing 41 constituting a first conduit leading through an integrated heat exchanger 40 constituting a heat exchange element. At one end, the tubing 41 comprises a heat exchanger inlet connection 33; at the other end the tubing 41 comprises a heat exchanger outlet connection 35. The heat exchanger connections constitute connections for attachment to a heat exchanger inlet and outlet, respectively, such as the inlet 32 and outlet 34 indicated in FIG. 2. When installed, the tubing 41 provides an intermediate passage 30 through the heat exchanger 40 and a perfusion system heat exchanger. The heat exchanger 40 further comprises a heater-cooler passage 46 constituting a second conduit with an entry port 36 and an exit port 38 for connection to a heater-cooler device.

The heat transfer device 301 comprises, along a length of the tubing 41, a fill port 42 and an integral pump 44. Instead of the pump 44, the tubing 41 may comprise a pump component for use with an external driver or a section of suitable characteristics for use with an external pump. For instance, the tubing 41 may comprise a section of sufficient length and flexibility for use with an external roller pump, or a centrifugal pump impeller arrangement for use with an external driver.

When installed to a heater-cooler device, temperature-controlled heater-cooler fluid may run via passage 46 to exchange heat with the intermediate fluid in the intermediate passage 30, as explained above, while fluidically isolating the heater-cooler fluid from the intermediate fluid and from the perfusion system heat exchanger.

The heat transfer device 302 shown in FIG. 5 comprises a heat exchanger plate 40b constituting a heat exchange element. The heat exchanger plate 40b is configured for coupling with a first heat exchanger plate 40a, which is configured for attachment to a heater-cooler device, in the manner described with reference to FIG. 3. The two plates 40a and 40b together provide heat transfer functionality from the heater-cooler fluid to an intermediate fluid while fluidically isolating the two fluids.

Figure 6:
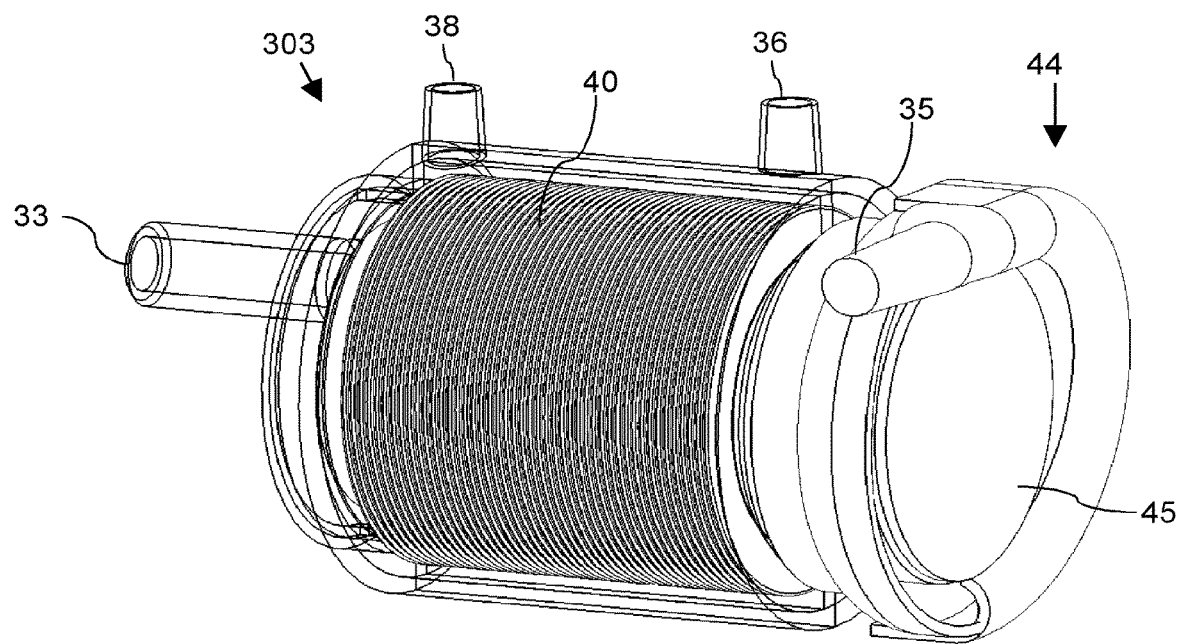
FIGS. 6 and 7 show a partially transparent isometric view and a section view, respectively, of a heat transfer device in accordance with another exemplary embodiment of the present invention.
Figure 7:
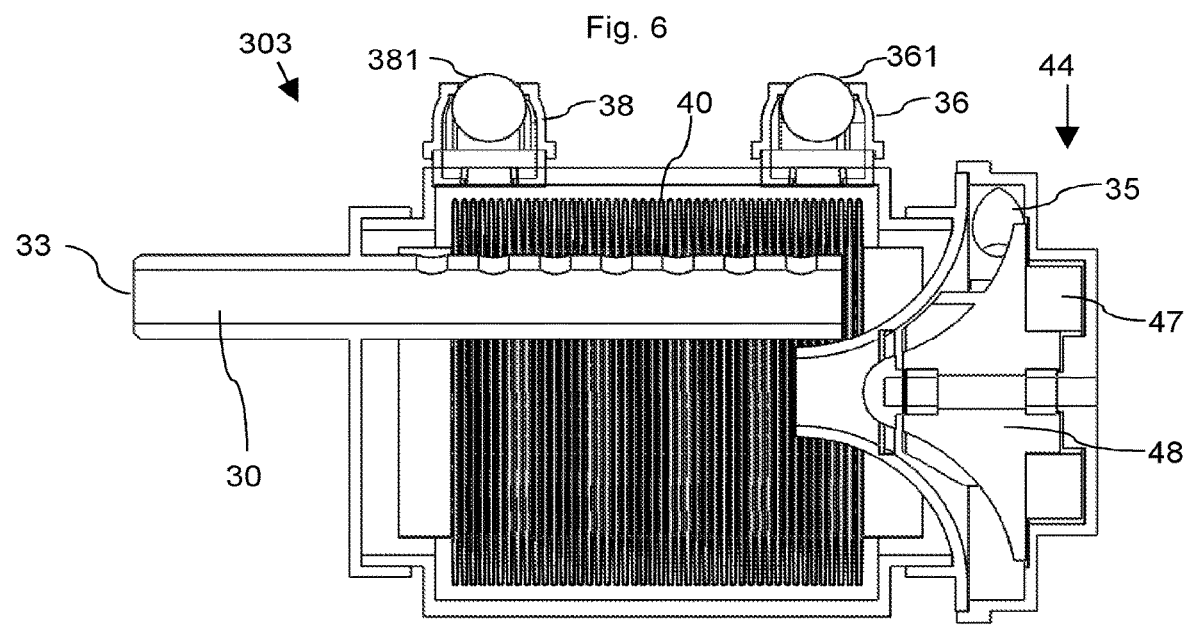

FIGS. 6 and 7 show a partially transparent isometric view and a section, respectively, of a heat transfer device 303 akin to the heat transfer device 301 shown in FIG. 4. The same reference numerals are used for equivalent elements in FIGS. 4, 6 and 7. The heat transfer device 303 comprises an entry port 36 and an exit port 38 for a heater-cooler fluid to be provided from a heater-cooler device to the intermediate heat exchanger 40 of the heat transfer device 303.

The heat transfer device 303 comprises an intermediate passage 30 leading from a heat exchanger inlet connection 33 to and heat exchanger outlet connection 35. The heat transfer device 303 comprises an impeller arrangement 45 of a centrifuge impeller, constituting a pump 44. The impeller arrangement 45 comprises a magnet 47 and an impeller 48 to be driven by an external drive mechanism, such as an electric motor (the external drive is not shown in FIGS. 6 and 7). When coupled with the external drive mechanism, the impeller arrangement 45 pumps the intermediate fluid from the inlet connection 33 to the outlet connection 35.

By virtue of quick-connect mechanisms, the entry port 36 and the exit port 38 can be detached from a heater-cooler device, and the inlet connection 33 and the outlet connection 35 can be detached from a perfusion system heat exchanger, such that the heat transfer device 303 is detachable from a heat exchange apparatus. The detached heat transfer device 303 can be disposed, avoiding the need for its sterilisation.

In embodiments, the heat transfer device 303 is intended for re-use and can be sterilised. In that case, the sterilisation can be performed independently of the operation of the heater-cooler device, e.g., off-site, without requiring sterilisation of the entire heater-cooler device.

As shown in FIG. 7, the entry port 36 comprises a ball sealing valve 361 constituting a non-return valve. Likewise, the exit port 38 comprises a ball sealing valve 381 constituting a non-return valve. The non-return valves help to contain heater-cooler fluid after disconnection of the heat transfer device 303. This reduces the risk of spillage of heater-cooler fluid, particularly when the heat transfer device 303 is detached quickly from the heater-cooler device. Likewise, the non-return valves may be provided in the inlet connection 33 or in the outlet connection 35, to help to contain non-sterile intermediate fluid.

Figure 8:
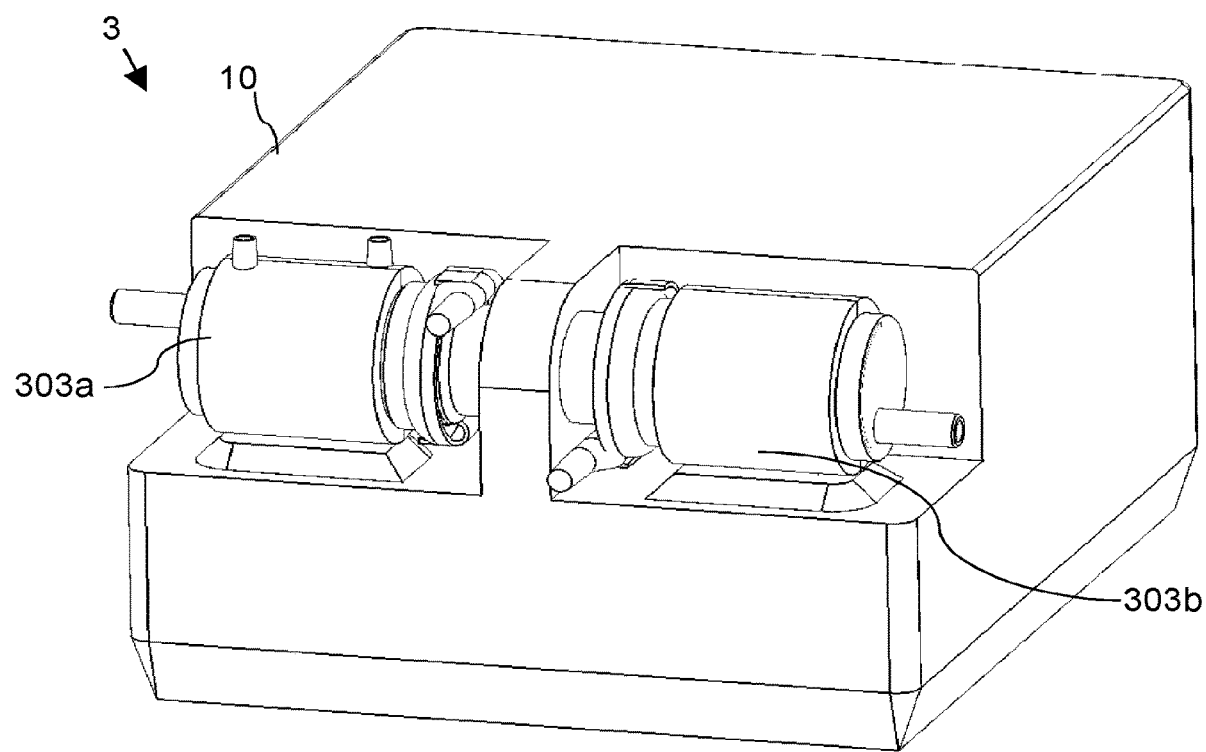
FIG. 8 shows an isometric view of components of a heater-cooler apparatus in accordance with an exemplary embodiment of the present invention.

FIG. 8 shows some of the components of a heater-cooler apparatus 3 comprising a heater-cooler device 10. The heater-cooler apparatus 3 corresponds conceptually to the heater-cooler apparatus 1 described above but may be coupled with two heat transfer devices 303a and 303b, each corresponding to the description of heat transfer device 303 above. Heater-cooler fluid of the heater-cooler device 10 is circulated through an intermediate heat exchanger of each of the heat transfer devices 303a and 303b to permit thermal exchange with an intermediate fluid to be pumped to a perfusion system heat exchanger (not shown in FIG. 8). The heat transfer device 303a may be used to provide an intermediate heat exchanger for an oxygenation line. The heat transfer device 303b may be used to provide an intermediate heat exchanger for a cardioplegia line. Each heat transfer device 303 can be removed and replaced individually. As the heater-cooler fluid is fluidically isolated from the intermediate passage of each heat transfer device 303, the need to disinfect the entire heater-cooler device 10 is reduced, and practically eliminated, if a fluid with antiseptic properties is used as heater-cooler fluid.

Figure 9:
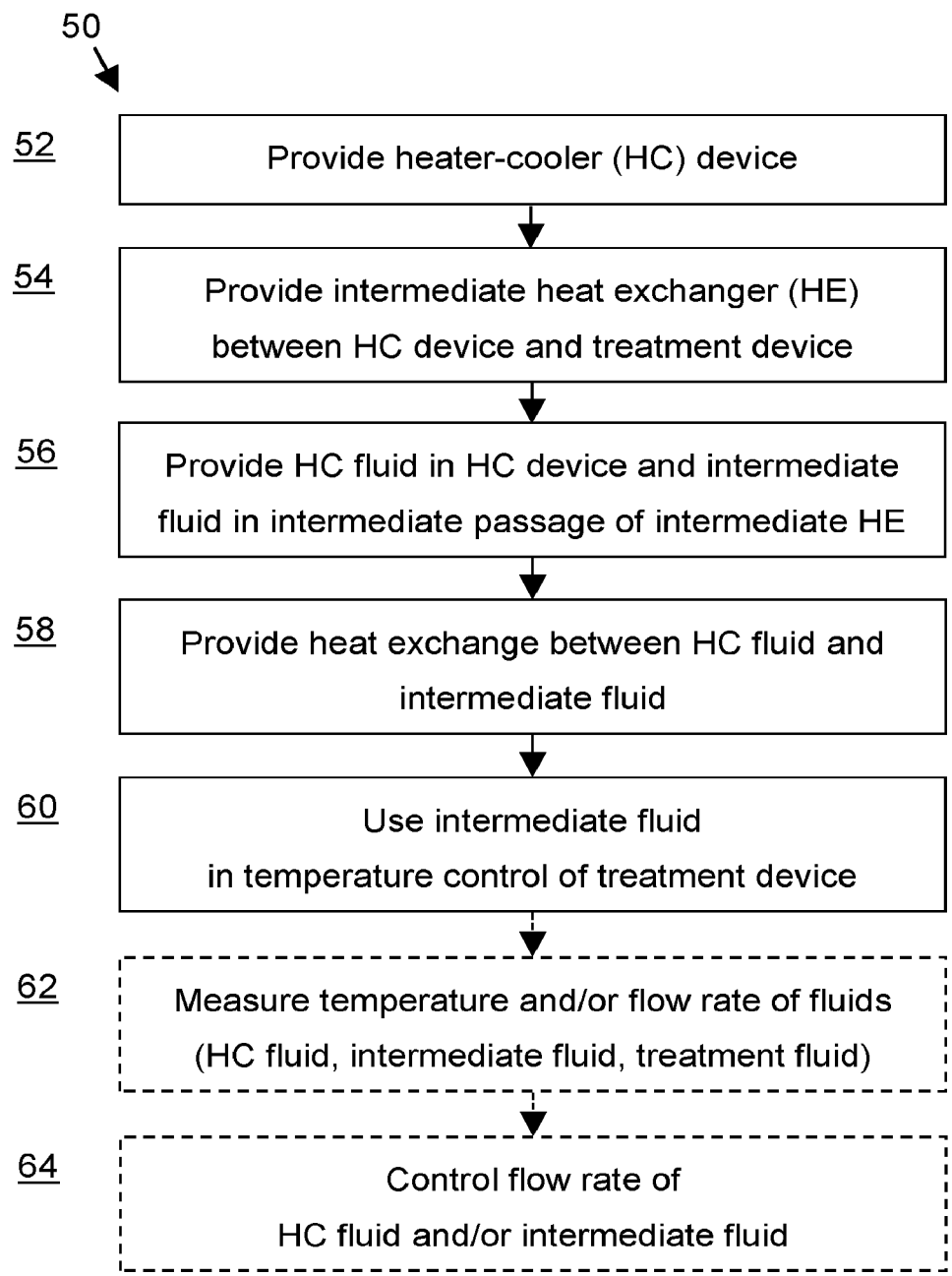
FIG. 9 shows steps of an exemplary sequence of method steps of a control method for controlling the temperature using a heater-cooler system in accordance with embodiments of the present invention.

The diagram in FIG. 9 shows an exemplary sequence of method steps of a control method 50 for controlling the temperature of a treatment device using a heater-cooler apparatus. The method comprises a step 52 of providing a heater-cooler device of a heater-cooler apparatus for controlling the temperature of an extracorporeal fluid passing through the treatment device. In step 54, an intermediate heat exchanger with an intermediate passage is provided between the heater-cooler device and the treatment device. The intermediate passage fluidically isolates the heater-cooler transfer fluid from the treatment device. In step 56, a heater-cooler fluid is provided in the heater-cooler device. The heater-cooler fluid may be an antiseptic fluid. Further, an intermediate fluid is provided in the intermediate passage. The intermediate fluid may be a different fluid than the heater-cooler fluid. For instance, the intermediate fluid may be a fluid chosen for its properties reducing wear of the coils in the heat exchanger of the treatment device. The intermediate fluid may be water.

In step 58, the heater-cooler fluid is circulated through the intermediate heat exchanger to permit thermal exchange with the intermediate fluid. The heat exchange mechanism may comprise a disposable heat exchanger as part of a disposable intermediate passage. The heat exchange mechanism may comprise a disposable heat exchanger component as part of a disposable intermediate passage. In step 60, the intermediate fluid is used to control the temperature of the treatment device.

In optional step 62, the temperature or the flow rate, or both the temperature and the flow rate, of one or more of the heater-cooler fluid, the intermediate fluid, and/or the treatment fluid are measured. The temperature and/or flow rate can be used to better control the heat transfer, and thus the temperature of the treatment fluid leaving the treatment device. In optional step 64, the flow rate of the heater-cooler fluid, of the intermediate fluid, or the flow rates of both the heater-cooler fluid and the intermediate fluid are controlled to better modulate the heat transfer at the treatment device. The control may comprise a closed-loop control mechanism with a set point temperature or heat transfer gradient.

Figure 10:
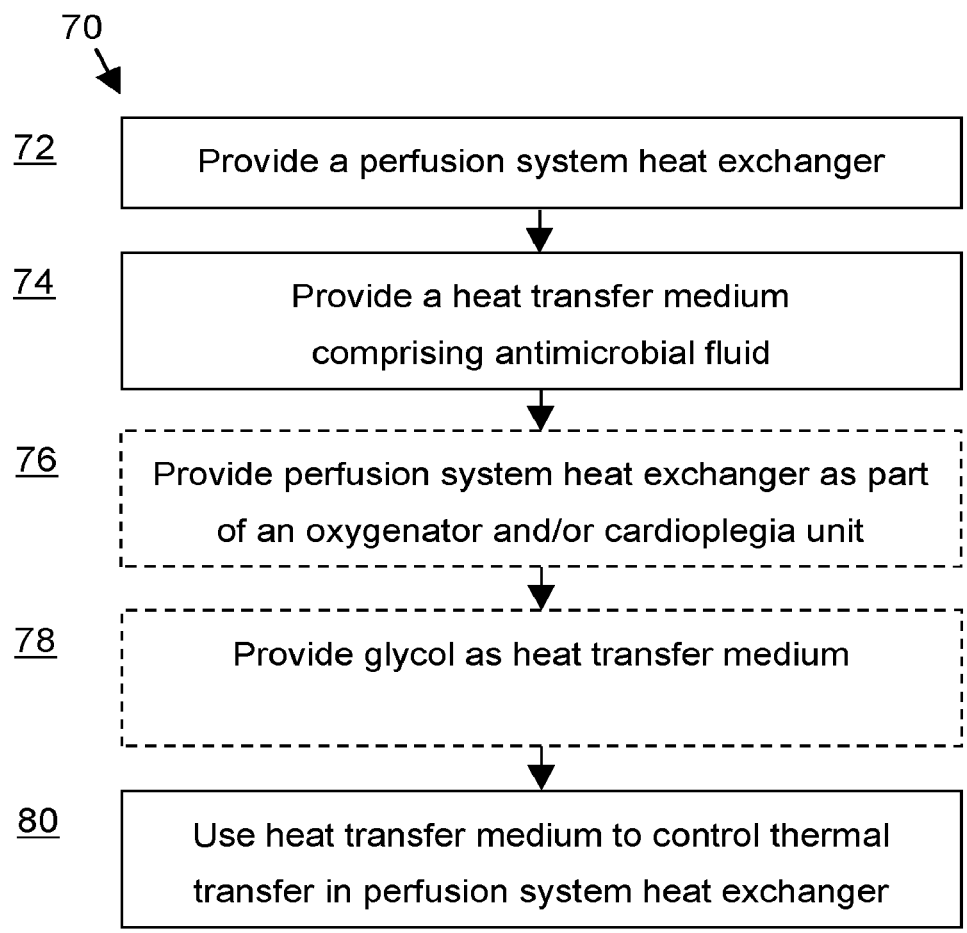
FIG. 10 shows steps of an exemplary sequence of method steps of a method of controlling thermal transfer in a perfusion system heat exchanger in accordance with embodiments of the present invention.

FIG. 10 shows a diagram setting out an exemplary sequence of method steps of a method 70 of controlling thermal transfer in a perfusion system heat exchanger. The method comprises a step 72 of providing a perfusion system heat exchanger. The perfusion system heat exchanger is part of an extracorporeal fluid treatment device for conditioning an extracorporeal patient fluid for administration to a patient. The perfusion system heat exchanger comprises a first fluid passage for a liquid heat transfer medium and a second fluid passage for the extracorporeal patient fluid to be temperature-controlled via exchange of thermal energy with the heat transfer medium.

In step 74, a heat transfer medium is provided through the first fluid passage of the perfusion system heat exchanger. The heat transfer medium comprises antimicrobial fluid. In an optional step 76, the perfusion system heat exchanger may be provided as part of an oxygenator, and/or as part of a cardioplegia delivery system. Likewise (not shown in FIG. 10), the perfusion system heat exchanger may be provided as a 'stand-alone' unit, to control the temperature of an extracorporeal fluid in a fluid line. In an optional step 78, glycol is provided as heat transfer medium. In step 80, the heat transfer medium is used to control the thermal transfer in the perfusion system heat exchanger, ie by flowing the heat transfer medium through the first fluid passage and by flowing the extracorporeal patient fluid to be temperature-controlled through the second fluid passage.

The expressions heat transfer fluid and thermal transfer fluid may be considered synonymous for the purposes of the present specification.

The invention claimed is:

1. A perfusion system comprising:
   a heater-cooler device for heating and/or cooling a heater-cooler fluid;
   an oxygenator for oxygenating blood;
   a cardioplegic agent delivery system for delivering cardioplegic agent to the blood;
   an oxygenation heat exchanger for controlling the temperature of oxygenated blood produced by the oxygenator;
   a cardioplegia heat exchanger for controlling the temperature of blood in the cardioplegic agent delivery system;
   an intermediate heat exchanger configured to permit heat exchange between the heater-cooler fluid and an antimicrobial heat exchange fluid, whereby the heater-cooler fluid is fluidically isolated from the oxygenation heat exchanger and from the cardioplegia heat exchanger; and
   a plurality of intermediate passages detachably connected to the oxygenation heat exchanger, the cardioplegia heat exchanger, and the intermediate heat exchanger to supply the antimicrobial heat exchange fluid to the oxygenation heat exchanger, the cardioplegia heat exchanger, and the intermediate heat exchanger.

2. The perfusion system in accordance with claim 1, wherein the intermediate heat exchanger comprises a first heat exchange element for integration with the heater-cooler device and a second heat exchange element integral with the intermediate passage.

3. The perfusion system in accordance with claim 1, wherein the intermediate heat exchanger and/or one or more of the intermediate passages comprises an arrangement preventing re-attachment to a heater-cooler device.

4. The perfusion system in accordance with claim 1, wherein the intermediate heat exchanger and/or one or more of the intermediate passages comprises a quick-connect mechanism for fluid connection with the heater-cooler device and/or for fluid connection with the perfusion system heat exchanger.

5. The perfusion system in accordance with claim 4, wherein the quick-connect mechanism comprises a self-sealing membrane.

6. The perfusion system in accordance with claim 1, further comprising a flow-control arrangement for controlling the flow rate of either or both of the heater-cooler fluid and the intermediate fluid.

7. The perfusion system in accordance with claim 6, wherein the flow-control arrangement comprises a roller pump, a centrifugal pump, or a centrifuge impeller arrangement for use with an external drive.

8. The perfusion system in accordance with claim 1, further comprising one or more non-return valves in each intermediate passage or in a heater-cooler conduit supplying the heater-cooler fluid.

9. The perfusion system in accordance with claim 1, further comprising a flow sensor arrangement for determining the flow rate of the heater-cooler fluid, of the intermediate fluid, and/or an extracorporeal patient fluid passing through the oxygenation heat exchanger.

10. The perfusion system in accordance with claim 1, further comprising a temperature sensor arrangement for determining the temperature of the heater-cooler fluid, of the intermediate fluid, and/or an extracorporeal patient fluid passing through the oxygenation heat exchanger.

11. The perfusion system in accordance with claim 1, wherein the intermediate heat exchanger and/or one or more of the intermediate passages comprises a fill port.

12. The perfusion system in accordance with claim 1, wherein the antimicrobial fluid is biocidal.

13. The perfusion system in accordance with claim 12, wherein the antimicrobial fluid comprises glycol.

14. The perfusion system in accordance with claim 13, wherein the glycol comprises propylene glycol or ethylene glycol.

15. The perfusion system in accordance with claim 1, wherein the oxygenation heat exchanger is part of a system capable of operating at sub-atmospheric pressure.

16. The perfusion system in accordance with claim 1, wherein the intermediate heat exchanger and/or one or more of the intermediate passages is disposable.

* * * * *